United States Patent
Johri et al.

(10) Patent No.: US 7,001,619 B2
(45) Date of Patent: Feb. 21, 2006

(54) **HEPATOCURATIVE EFFECT OF *EMBLICA OFFICINALIS* AGAINST CYP 450 BIO-ACTIVATION HEPATOTOXICITY OF DRUGS**

(75) Inventors: Rakesh Kamal Johri, Jammu (IN);
Sheikh Tasaduq Abdullah, Jammu (IN); Kuldeep Singh, Jammu (IN);
Devinder Kumar Gupta, Jammu (IN);
Bal Krishan Kapahi, Jammu (IN);
Dilip Manikrao Mondhe, Jammu (IN);
Satinder Mohan Jain, Jammu (IN);
Om Parkash Suri, Jammu (IN);
Kasturi Lal Bedi, Jammu (IN);
Ghulam Nabi Qazi, Jammu (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 10/106,119

(22) Filed: Mar. 27, 2002

(65) Prior Publication Data

US 2003/0185922 A1  Oct. 2, 2003

(51) Int. Cl.
*A61K 9/00* (2006.01)
*A61K 9/20* (2006.01)
*A61K 35/00* (2006.01)
*A61K 35/78* (2006.01)

(52) U.S. Cl. ............... 424/725; 424/400; 424/464
(58) Field of Classification Search ............ 424/464, 424/400, 725
See application file for complete search history.

(56) References Cited

U.S. PATENT DOCUMENTS

| | | | | |
|---|---|---|---|---|
| 5,658,913 A | * | 8/1997 | Kim et al. | 514/255 |
| 6,124,268 A | * | 9/2000 | Ghosal | 514/27 |
| 6,362,167 B1 | * | 3/2002 | Ghosal | 514/25 |
| 2002/0156653 A1 | * | 10/2002 | Florio et al. | 705/3 |

* cited by examiner

*Primary Examiner*—Thurman K. Page
*Assistant Examiner*—Simon J. Oh
(74) *Attorney, Agent, or Firm*—Smith, Gambrell & Russell, LLP

(57) ABSTRACT

The present invention relates to a composition useful for hepatocurative effect against CYP 450 bio-activation hepatotoxicity induced by drugs, said composition comprising an extract from *Emblica officinalis* and optionally pharmaceutically acceptable additives and method of treating drug induced hepatotoxicity.

12 Claims, 6 Drawing Sheets

*Emblica Officinalis*

HEPATOCURATIVE EFFECT OF EMBLICA OFFICINALIS AGAINST CYP 450 BIO-ACTIVATION HEPATOTOXICITY OF DRUGS

FIELD OF THE PRESENT INVENTION

The present invention relates to a composition useful for hepatocurative effect against CYP 450 bio-activation hepatotoxicity induced by drugs, said composition comprising an extract from *Emblica officinalis* and optionally pharmaceutically acceptable additives and method of treating drug induced hepatotoxicity.

BACKGROUND OF THE PRESENT INVENTION

Liver disorders are still the major health hazards both in urban and rural areas of the world. Despite scientific advances in our understanding of hepatotoxicity, and leads provided by traditional system of medicine, we do not have yet any effective entities to cure liver derangement more importantly those which are caused by a variety of drugs. The Indian Council of Medical Research, New Delhi in its revised research programme on traditional medicines, has adopted liver diseases as one among six thrust areas for multidisciplinary study.

The disorders of the liver may be classified into acute or chronic hepatitis (inflammatory liver diseases), hepatosis (non-inflammatory disorders). The acute condition is often followed by liver cirrhosis as well as hepatic coma with grave prognosis. Liver cirrhosis as such accounts amongst the ten top fatal diseases in the world. Exposure of humans to a variety of agents such as chemicals and drugs (xenobiotics), many natural compounds, viral and bacterial pathogens with attendant predisposable conditions, etc. are considered responsible for hepatic insufficiency.

There are large group of drugs which on repeated administration produce liver toxicity. These are mediated primarily by bioactivation so that the products of parent drug are toxic. Another class of drugs induce toxicity by causing membrane rupture or DNA damage and by interfering with protein synthesis. One of the important categories of drugs are the anti-TB drugs which when taken regularly cause hepatotoxicity.

Tuberculosis is prevelent in all counteries of the world—tropical, subtropical and colder regions. The chemotherapy of tuberculosis is important and challenging, because the disease is often chronic and the toxicity due to anti-TB drugs pose therapeutic problems. The disorders of the liver caused during the treatment of tuberculosis, by known antimicrobial agents range from jaundice to the fibrosis of the liver. Several cases progress to the chronic form of disease or have a fulminant course and prove fatal. Three drugs i.e., rifampicin, pyrazinamide and isoniazid comprise first choice treatment of tuberculosis. These are to be administered for long period of time and produce liver dysfunction leading to toxicity.

Jaundice is amongst the most prominent incidence of their adverse raections. The characteristic pathology is the bridging and multilobular necrosis. Hypersensitivity to these drugs leads to hepatitis. Multidrug treatment also poses special problems. Rifampicin causes liver damage. Disturbances in liver function is more if it is combined with isoniazid. Pyrazinamide is the most toxic of the three anti-TB drugs. Continuation of the drugs in combination after symptoms of hepatic dysfunction have appeared tends to increase further the severity of damage. Severe hepatic injury leading to death has been reported in patients receiving these drugs (Slivka, I L, Farmakol Toksikol-1989: 52;82–85)

In our traditional system of medicines (Ayurveda), use of several medicinal plants have been prescribed for alleviating liver disorders. There are nearly forty indigenous polyherbal formulations from more than 100 plants enjoying reputation of being hepatoprotectives. However, none have been specified as a therapeutic agent, which is able to protect the liver from injury due to treatment of anti-TB drugs. This owes partly to the fact that reports are scanty with regard to evaluation of plants/plant products, which would seem focussed specially against hepatic injury caused by drugs which produce toxicity as a result of bioactivation.

There is thus a growing interest in the development of herbal entities considered relatively safe for alleviating liver disorders specifically caused by the anti-TB drugs.

*Emblica officinalis* Gaertn. (Hindi: Amla) (Euphorbiaceae) is widespread in India, Ceylon, Malaya and China. The tree is common in mixed deciduous forests of India ascending to 4500 ft on the hills, cultivated in gardens and homeyards. It is a small or medium sized deciduous tree, fruits depressed globose, ½ to 1 inch in diameter, fleshy, and contains six trigonows seeds. The fruit is sour and is occasionally eaten raw. The fruit pulp contains (%); moistre 81.2, protein 0.5, fat 0.1, mineral matter 0.7, Ca 0.005, Phosphorus 0.02 and Iron 1.2 mg/100 gm, nicotinic acid 0.2 mg/100 gm, vitamin C 600 mg/100 mg. (Medicinal plants of India, Satyavati et al (ed.), ICMR, new Delhi, 1976, p 377). The potent vitamin C-like activity has been located in the low molecular weight hydrolysable tannins. Four such compounds emblicanin-A, emblicanin-B, punigluconin and pedunculagin have been isolated from the fresh pericarp. The first two compounds are naturally occurring galloellagitannins (Ghosal, et al, IndJChem, 1996:353:941–948; Bhattacharya et al, Phytomedicine, 2000: 7: 173–175)

The fruit is acrid, cooling, and diuretic. Dried fruit is useful in haemorrhage, diarrhoea and dysentry. It has been extensively use in anemia, liver diseases and dyspepsea. A fermented liquor prepared from the fruits is used in jaundice. Fruits are a reputed Ayurvedic rasayan (revitaliser, biological response modifier) (Sharma P. V. Dravyaguna vijnana, Chaukhamba Sanskrit Sansthan, Varanasi, 1978). Several pharmacological properties are also reported. Leaf extracts have been found to be anti-inflammatory (Summanen et al, Planta Medica, 1993:59: 666), antioxidant (Jose. and Kuttan, Clin. Biochem. Nutr, 1995:19:63–70), hypolipidemic (Mathw:eta\,JEthnopharmacol, 1996:50:61–68), cell growth inhibition (Psatima et al, ACS Symp. Ser, 1998, p701). Hepatoprotective activity of *Emblica officinalis* extracts against a chemical viz., carbon tetrachoride induced liver toxicity has been demonstrated (Jose J K & Kutten R, J. Ethnopharmacology 2000:72; 135–40; Bhattacharya et al, Phytomerdicine 2000:7:173–5).

The article by Sharma et al (Hum Exp. toxicol 2000:19; 337–84) suggests that *Emblica Officinalis* prevents genotoxicity induced by benzopyrines. Benzopyrene is one of the prominent environmental carcinogen which is a specific substrate for CYP 450 1A1. Both are clastogenic. However, the liver toxicity produced by the drugs including anti-TB drugs is dependent on a great measure to their bio-activation through multiple CYP isoforms, the most prominent being CYP450 3A4. There are several agents, which reduce CYP levels or reverse the micronuclei formation but are not hepatoprotective. To cite an example, applicants have developed a molecule, piperine which is a specific inhibitor of CYP 450 1A1, but is not hepatoprotective. Similarly, there are several known compounds, which reverse the genotoxicity but are not hepatoprotective. Therefore the decrease in CYP 1A1 or reversal of clastrogencity can not be construed as hepatoprotection. For example, jaundice (hepato-biliary dysfunction) has not been correlated with genotoxicity, rather it may be an early event in the onset of liver toxicity. In the present article, a casual relationship between CYP decrease or genotoxicity has not been related to attenuation of clinical pathology usually seen in symptoms of hepatotoxicity.

In the present invention, the Applicants provide protection against hepatotoxicity produced by all such drugs, which are bio-activated by multiple CYP isoforms as indicated by clinical parameters in serum/liver. Besides, we claim that the clinical parameters showing toxicity are reversed even if the symptoms of genotoxicity may not begin to appear. For example decrease in abnormal rise of serum Bilirubin, which may be attributed to a protective effect also due to other cellular factors such as membrane stabilization, as revealed in primary monolayer cultures of liver cells.

Thus, we claim preparations from *Emblica officinalis* which are superior so far as their systemic effects are manifested in clinical profile (serum/liver parameters) which correlate to their hepatoprotective profile.

OBJECT OF THE PRESENT INVENTION

The main object of the present invention is to develop a hepatocurative composition against CYP 450 bio-activation hepatotoxicity induced by drugs.

Another main object of the present invention is to develop a hepatocurative composition against CYP 450 bio-activation hepatotoxicity induced by anti-TB drugs.

Yet another object of the present invention is to develop a composition from fruit *Emblica officinalis* for hepatocurative effect.

Still another object of the present invention is to develop a composition from fruit *Emblica officinalis* for hepatocurative effect against CYP 450 bio-activation hepatotoxicity.

Still another object of the present invention is to develop a method of preparing an extract from fruit *Emblica officinalis*.

Still another object of the present invention is to develop a method for treating a subject for CYP 450 and free radical mediated hepatotoxicity caused by drugs using composition comprising an extract from *Emblica officinalis*.

Still another object of the present invention is to develop a method of using hepatocytes to understand the effect of extract from fruit *Emblica officinalis*.

SUMMARY OF THE INVENTION

The present invention relates to a composition useful for hepatocurative effect against CYP 450 bio-activation hepatotoxicity induced by drugs, said composition comprising an extract from *Emblica officinalis* and optionally pharmaceutically acceptable additives and method of treating drug induced hepatotoxicity.

DETAILED DESCRIPTION OF THE PRESENT INVENTION

Accordingly, the present invention relates to a composition useful for hepatocurative effect against CYP 450 bio-activation hepatotoxicity induced by drugs, said composition comprising an extract from *Emblica officinalis* and optionally pharmaceutically acceptable additives and method of treating drug induced hepatotoxicity.

In one embodiment of the present invention, a composition useful for hepatocurative effect against CYP 450 bio-activation hepatotoxicity induced by drugs, said composition comprising an extract from *Emblica officinalis* and optionally pharmaceutically acceptable additives.

In another embodiment of the present invention, wherein said additives are selected from a group of nutrients comprising proteins, carbohydrates, sugar, talc, magnesium stearate, cellulose, calcium carbonate, starch-gelatin paste, and/or pharmaceutically acceptable carrier, excipient, diluent, or solvent.

In yet another embodiment of the present invention, wherein said composition is administered orally.

In still another embodiment of the present invention, wherein said extract and additives are in the ratio ranging between 1:1 to 1:10.

In still another embodiment of the present invention, wherein said additives have no effect on the hepatocurative effect of the said extract.

In still another embodiment of the present invention, wherein said extract is prepared in a solvent selected from a group comprising aqueous, aqueous-ethanolic, ethanolic, ketonic, ethereal, halogenated solvents.

In still another embodiment of the present invention, wherein said composition shows tanin content in the range of 8.5 to 15%.

In still another embodiment of the present invention, wherein, said composition for the oral route is in form of capsule, tablet, syrup, concentrate, powder, granule, aerosol, and/or beads.

In further another embodiment of the present invention, a method of preparing composition comprising an extract from *Emblica officinalis* and optionally pharmaceutically acceptable additives, said method comprising steps of adding polar solvent to the fruit *Emblica Officinalis* to obtain the extract and optionally adding pharmaceutically acceptable additives.

In another embodiment of the present invention, wherein said fruit is incubated with polar solvent at room temperature for about 15–25 hours.

In yet another embodiment of the present invention, wherein said extract is from fresh and/or semi dried fruits of *Emblica Officinalis*.

In still another embodiment of the present invention, wherein said extract and additives are in the ratio ranging between 1:1 to 1:10.

In still another embodiment of the present invention, wherein said extract is prepared in a solvent selected from a group comprising aqueous, aqueous-ethanolic, ethanolic, ketonic, ethereal, halogenated solvents.

In still another embodiment of the present invention, wherein, said composition for the oral route is in form of capsule, tablet, syrup, concentrate, powder, granule, aerosol, and/or beads.

In further embodiment of the present invention, a method of treating a subject for CYP 450 and free radical mediated hepatotoxicity caused by drugs using composition comprising an extract from *Emblica officinalis* and optionally pharmaceutically acceptable additives.

In another embodiment of the present invention, introducing drug toxicity in hepatocytes.

In yet another embodiment of the present invention, adding said composition to said hepatocytes exposed to drug hepatotoxicity.

In still another embodiment of the present invention, measuring changes in the level of liver/serum markers to estimate hepatocurative effect of the said composition.

In still another embodiment of the present invention, wherein said method is particularly effective against hepatotoxicity caused by anti-TB drugs.

In still another embodiment of the present invention, wherein said composition is not effective against hepatotoxicity which is independent of bio-activation by CYP 450.

In still another embodiment of the present invention, wherein said composition is administered orally.

In still another embodiment of the present invention, wherein, said composition for the oral route is in form of capsule, tablet, syrup, concentrate, powder, granule, aerosol, and/or beads.

In still another embodiment of the present invention, wherein said composition is useful for treating animals or human beings.

In still another embodiment of the present invention, wherein said composition has no adverse effect on health.

In still another embodiment of the present invention, wherein said drugs are selected from a group comprising Paracetamol, $CCl_4$, and anti-TB drugs.

In still another embodiment of the present invention, wherein said anti-TB drugs are selected from a group comprising Rifampicin, Pyrazinamide, and isoniazid.

In still another embodiment of the present invention, wherein said composition controls abnormal rise in the clinical pathological symptoms revealed by serum/liver markers serving as indices of hepatic damage besides control of high levels of Bilirubin.

In still another embodiment of the present invention, wherein said method uses hepatocyte culture for ideal insight.

In still another embodiment of the present invention, wherein said drugs is used at cytotoxic levels to produce valid and reproducible results in liver cells.

In still another embodiment of the present invention, wherein said composition is useful for treating animals or human beings.

In still another embodiment of the present invention, wherein said composition has no adverse effect on health.

In still another embodiment of the present invention, wherein said composition shows restoration of hepatocyte viability.

In still another embodiment of the present invention, wherein said method shows prevention of cell membrane leakage.

In still another embodiment of the present invention, wherein said composition shows about 96% hepatocurative effect against combined effect of anti-TB drugs of Rifampicin, and Isoniazid.

In still another embodiment of the present invention, wherein said composition reverses the leakage of glutamate pyruvate transaminase (GPT) from hepatocyte.

In still another embodiment of the present invention, wherein said composition shows hepatocurative effect of about 96% against combined effect of anti-TB drugs of Rifampicin, isoniazid, and pyrazinamide.

In still another embodiment of the present invention, wherein said composition shows about 94% hepatocurative effect against rise in lipid Peroxidation (LPO) induced by combination of anti-TB drugs Rifampicin, isoniazid, and pyrazinamide.

In still another embodiment of the present invention, wherein said composition shows about 96% decrease of serum Bilirubin as a hepatocurative effect against combination of anti-TB drugs Rifampicin, isoniazid, and pyrazinamide.

In still another embodiment of the present invention, wherein said method helps restore liver function to normal.

In still another embodiment of the present invention, wherein dosage of said composition is ranging between 50–250 mg/kg.

In still another embodiment of the present invention, wherein said method is used for hepatocurative effect against drugs causing liver dysfunction, including anti-TB drugs.

In further embodiment of the present invention, the applicants provide protection against hepatotoxicity produced by all drugs, which are bio-activated by multiple CYP isoforms as indicated by clinical parameters in serum/liver. Besides, we claim that the clinical parameters showing toxicity are reversed even if the symptoms of genotoxicity may not begin to appear. For example decrease in abnormal rise of serum Bilirubin, which may be attributed to a protective effect also due to other cellular factors such as membrane stabilization, as revealed in primary monolayer cultures of liver cells.

Further, applicants have made use of their expertise and years to research to establish that *Emblica Officinalis* (Alma) cures hepatotoxicity induced by drugs that is restricted to CYP 450 bio-activation hepatotoxicity.

Thus, applicants claim preparations from *Emblica officinalis* which are superior so far as their systemic effects are manifested in clinical profile (serun/liver parameters) which correlate to their hepatoprotective profile.

In further embodiment of the present invention, it relates to preparations and methods of preparation and use of such products which restores the normal liver function against drug induced toxicity as a result of bio-activation of drugs applicable with particular relevance to anti-TB drug(s) induced liver toxicity. The compositions and methods of the present invention increase biological defence mechanism of the tissue, improve recovery from dysfunctional states of the liver after prolonged challenge of anti-TB drugs.

In another embodiment of the present invention, the compositions and methods of the present invention contain one of the extracts/fractions of *Emblica officinalis* fruit as an essential ingredient. These extracts/fractions may be obtained from fresh or semi dried fruits of *Emblica officinalis*. The compositions are formulated with more than one extracts and combined in any weight ratios. The preferred weight ratios include 1:1,1:2,1:1:1:, 1:2:2.2:1:2:, 2:2:1.

In still another embodiment of the present invention, it is related to preparation and use of products from *Emblica officinalis*, which restores normal liver function against drug induced toxicity caused as a result of bio-activation of drugs applicable with particular relevance to anti-TB drug(s) induced liver toxicity. The products of the invention comprise aqueous, aqueous-ethanolic, ethanolic, ketonic, ethereal, halogenated solvents extracts/fractions from *Emblica officinalis*, obtained either from fresh or semi-dried fruits. These contain 8.5–15% of tannin content. It also relates to preparation of compositions of such products in different proportions of more than one ingredient. These products either alone or in combination are intended to be used against drug induced liver toxicity as represented by specific mechanism underlying liver disorders and usually manifested in clinical conditions of liver dysfunction.

In still another embodiment of the present invention, the preparations either alone or in composition are also intended to be used against anti-TB drug(s).The use of such products as developed in the present invention controls the abnormal rise in clinical pathological symptoms revealed by serum/liver markers serving as indices of hepatic damage besides control of high levels of Bilirubin.

In still another embodiment of the present invention, in the development of the present invention the ample information has been utilized which exists regarding the advances in our understanding of mechanisms responsible for hepatotoxic injury due to drugs. More importantly the choice of a suitable model for the evaluation of anti-toxic profile of any substance is also crucial.

In still another embodiment of the present invention, a large body of information has been gained in favor of the present invention by using liver cell (hepatocyte) cultures, which ideally provide an insight into the mechanism of a toxin-induced impairment of hepato-biliary dysfunction because this model allows use of a test compounds (such as anti-TB drugs) to be used at cytotoxic level so that a valid and reproducible toxicity is generated. The in vitro cell culture model is of significant interest in ascertaining the mechanisms of toxicity and its reversal by protective agents.

In still another embodiment of the present invention, liver cells are considered as system of choice which have found ample application in the evaluation of cyto- cum genotoxicity of chemicals and drugs (Nakagawa and Tayama, Arch Toxicol, 1995:69:208) and as such have been used in the evaluation of hepatoprotective profiles of the present invention. The mechanisms are revealed in critical biochemical functions of liver cells which are sensitive indicators of drug (s) toxicity. (Tomasi et al, Toxicol/Vtf/zo/:15: 178–183). Both cellular lysis (measured by leakage of transaminases enzymes and lactated dehydrogenase from the cells) and the metabolic competence of the tissue are modified as a function of both the duration and concentration of the drugs (Goethals et al Fundm Appl Toxicol 1984:4:441–450).

In still another embodiment of the present invention, the preparations (alone or in combination) act in a specific manner. These act against toxicity produced by drugs including anti-TB drugs which require bioactivation by hepatic cytochrome P 450 dependent mixed function oxidases. Cytochrome P450 have been shown to be involved in the liver toxicity (Anundi I, Lindros K O, Pharmacol Toxicol 1992; 70;453–458). Participation of CYP 450 dependent oxidation of drugs including anti-tubercular drugs rifampicin, isoniazid, pyrazinamide in liver is reported (Ono et al, Biol Pharm Bull 1998:21:421–425).

In still another embodiment of the present invention, that the preparations mentioned in the present invention act in a specific manner is further evidenced by the observation that these preparations have not been found effective against galactosamine induced toxicity which is not dependent upon the intervention of mixed function oxidases. Of serious concern is the toxicity produced by use of some drugs in combination such as anti-tubercular drugs. Preparations alone or in combination, prevent not only (a) rifampicin (b) isoniazid (c) pyrazinamide induced toxicity but also various combinations of these such as (a) rifampicin+isoniazid (b) rifampicin+pyrazinamide (c) isoniazid+pyrazinamide and (d) rifampicin+isoniazid+pyrazinamide toxicity. The metabolic activation of drugs including anti-TB drugs alone or in combination is also accompanied by reactive intermediates which may be free radical/active metabolites/free oxy radicals through a variety of cellular oxidative metabolic pathways. An altered oxidative/antioxidative profile is closely associated with production of drug (s) induced hepatic injury (Sodhi et al, Hum Exp Toxicol 1997; 16;315–321). The efficacy of the products of the present invention is further shown by their anti-lipoperoxidant (anti-oxidant) profile. By using the preparations of the present invention a decrease in the accumulation of excess levels of the product of oxygen metabolism has been revealed.

In still another embodiment of the present invention, also included are the preventing role of the products developed herein, against cell membrane leakage and restoration of cell viability in challenged liver tissues caused as a result of toxic menifestations. Preparations act in a specific manner in as much as they prevent toxicity produced by bioactivation of drug (s) and combination of drugs (s) as described in the above art. The products described have no cytotoxicity and on the other hand enhance overall biological defense systems per se.

BRIEF DESCRIPTION OF THE ACCOMPANYING DRAWINGS

FIG. 1 shows liver toxicity wherein plant extract attenuates Rifampicin induced hepatotoxicity by restoring liver function to normal (95% effect). The cell toxicity indicators shown in the said FIG. 1 is the leakage of lactate dehydrogenase (LDH) from intact cells after toxin challenge and its reversal by extracts.

FIG. 2 shows leakage of glutamate pyruvate transaminase wherein said plant extracts in combination attenuates Rifampicin+isoniazid induced hepatotoxicity by restoring liver function to normal (96%). The cell toxicity indicators shown in FIG. 2 is the leakage of glutamate pyruvate transaminase (GPT) from intact cells after toxin challenge and its reversal by the extracts in combination. (Model: primary monolayer cultures of liver cells).

FIG. 3 shows leakage of serum glutamate pyruvate transaminase (GPT) after toxin challenge and its reversal by *Emblica officinalis* fraction wherein *Emblica officinalis* reverses Rifampicin+isoniazid+pyrazinamide induced hepatotoxicity and restores the liver function to normal (96%). The cell toxicity indicators shown in FIG. 3 is the leakage of serum glutamate pyruvate transaminase (GPT) after toxin challenge and its reversal by *Emblica officinalis* fraction.

FIG. 4 shows that fractions provide 96% protection against cell leakage as measured by serum GPT levels and increases cellular defense. 75% increase in glutathione levels (liver) is observed.

FIG. 5 shows 94% protection against rise in lipid Peroxidation (LPO, liver) and 96% decrease of serum Bilirubin in response to treatment with extract of the present invention.

EXAMPLES

The invention of instant Application is further illustrated by the following examples, which should not, however be construed to limit the scope of the invention. The following examples are not intended to be limiting in any way, but demonstrate some of the preferred embodiments of the present invention. Any person skilled in the art can design more combinations useful against drug-induced toxicity, which may be considered as part of the present invention.

Example 1

Table 1 shows that the plant products are effective against paracetamol hepatotoxicity which is mainly dependent against bioactivation mechanisms mediated by CYP 450. % protection is shown as combined effect release of LDH and GPT in serum.

TABLE 1

Effect of plant products against hepatotoxicity produced by paracetamol

| Treatment | paracetamol |
|---|---|
| Toxicity | 93% |
| % protection as measured by combined effect against LDH and GPT leakage | |
| Extract | 97% protection |
| Fraction | 96% protection |

Example 2

Table 2 shows that the preparations of the present invention are not effective against liver toxicity produced by agents where the toxicity is primarily not dependent on bioactivation by CYP 450.

TABLE 2

Effect of plant products against hepatotoxicity produced by galactosamine.

| Treatment | galactosamine |
|---|---|
| Toxicity | 93% |
| % protection as measured by combined effect against LDH and GPT leakage | |
| Extract | 3% |
| Fraction | 7% |

Example 3

Figure 1:
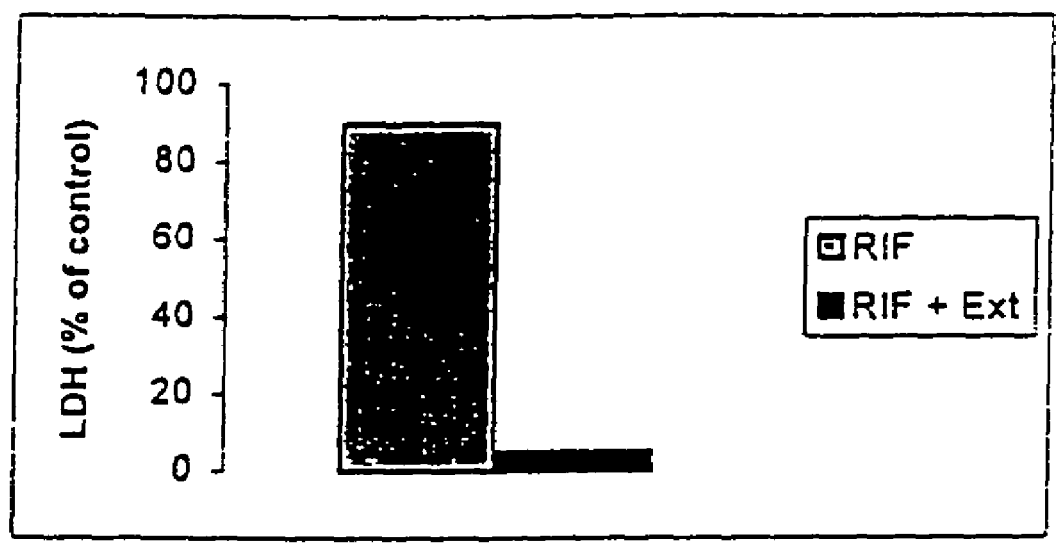

Plant extract attenuates Rifampicin induced hepatotoxicity by restoring liver function to normal (95% effect). The cell toxicity indicators shown in FIG. 1 is the leakage of lactate dehydrogenase (LDH) from intact cells after toxin challenge and its reversal by extracts. (Model; primary monolayer cultures of liver cells)

Example 4

Figure 2:
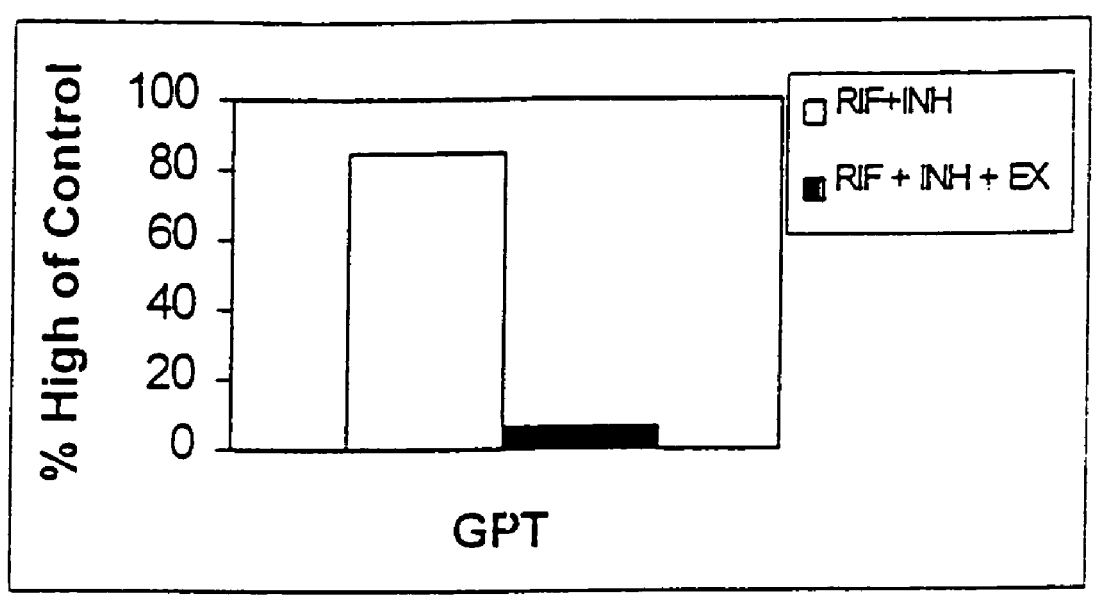

Plant extracts in combination attenuates Rifampicin+isoniazid induced hepatotoxicity by restoring liver function to normal (96%). The cell toxicity indicators shown in FIG. 2 is the leakage of glutamate pyruvate transaminase (GPT) from intact cells after toxin challenge and its reversal by the extracts in combination. (Model: primary monolayer cultures of liver cells).

Example 5

Figure 3:
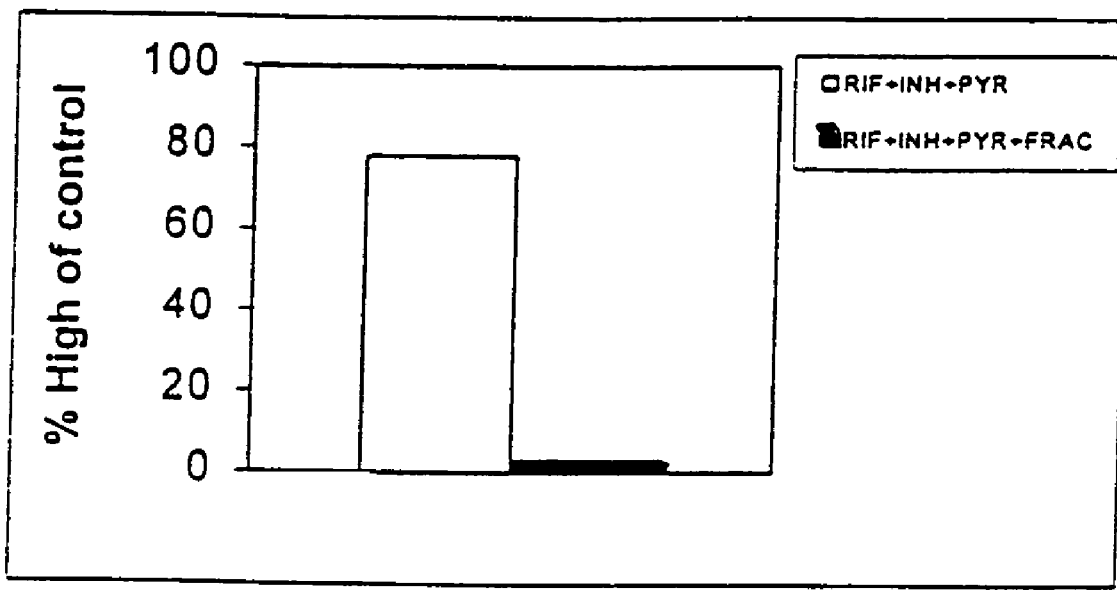

*Emblica officinalis* reverses Rifampicin+isoniazid+pyrazinamide induced hepatotoxicity and restores the liver function to normal (96%). The cell toxicity indicators shown in FIG. 3 is the leakage of serum glutamate pyruvate transaminase (GPT) after toxin challenge and its reversal by *Emblica officinalis* fraction.

Example 6

Figure 4:
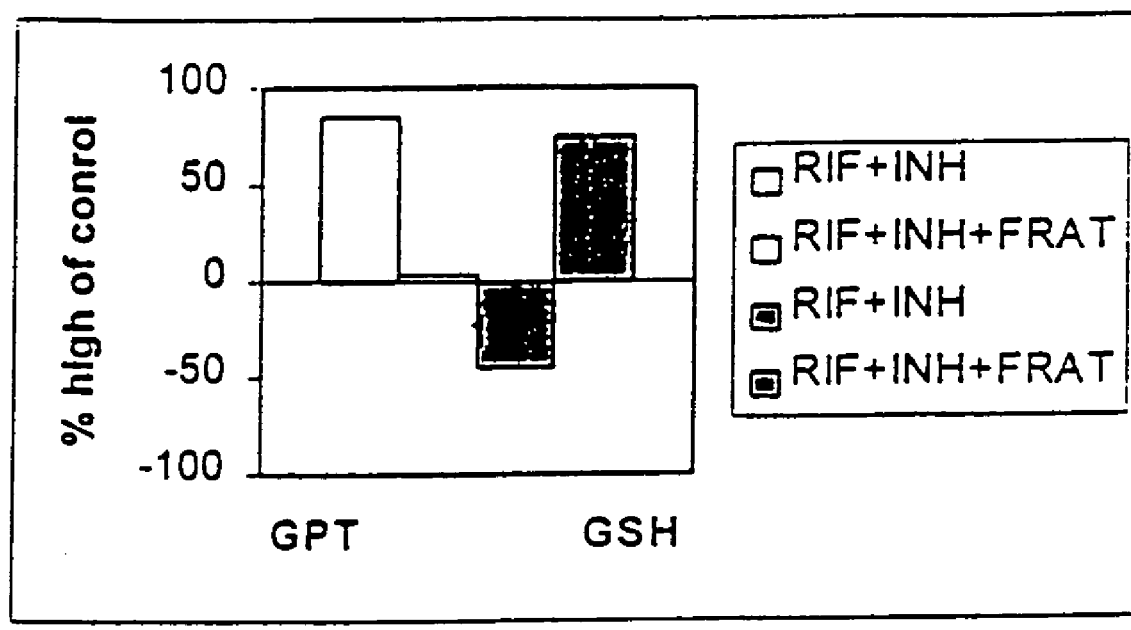
FIG. 4 shows protection against cell leakage wherein, *Emblica officinalis* fractions in combination prevents Rifampicin+isoniazid induced toxicity.

*Emblica officinalis* fractions in combination prevents Rifampicin+isoniazid induced toxicity. FIG. 4 shows that fractions provide 96% protection against cell leakage as measured by serum GPT levels and increases cellular defense. 75% increase in glutathione levels (liver) is observed.

Example 7

Figure 5:
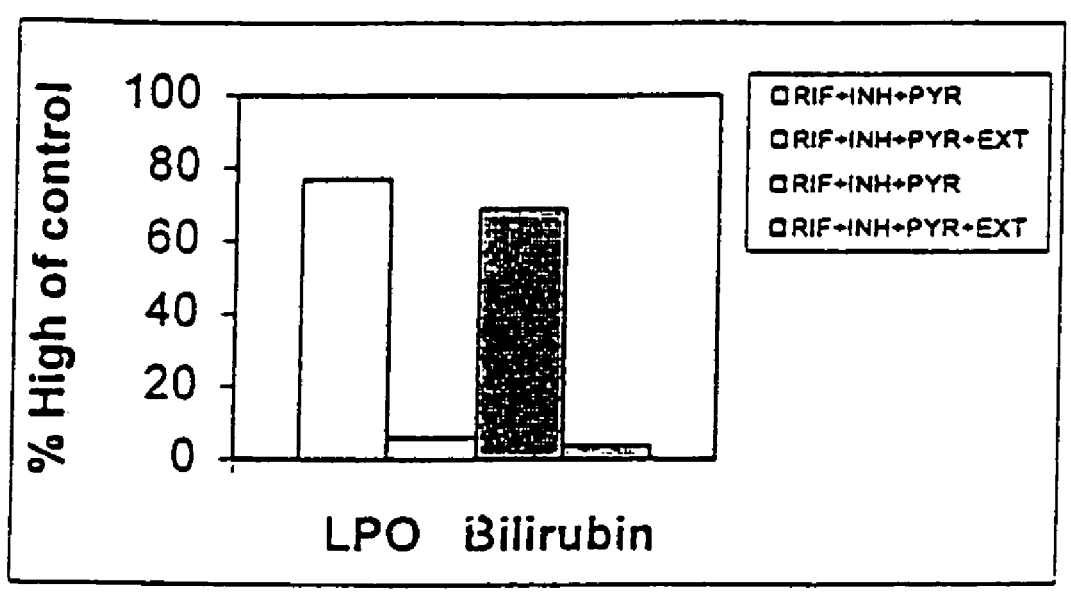
FIG. 5 shows *Emblica officinalis* extract reverses Rifampicin+isoniazid+pyrazinamide induced toxicity.
Figure 6:
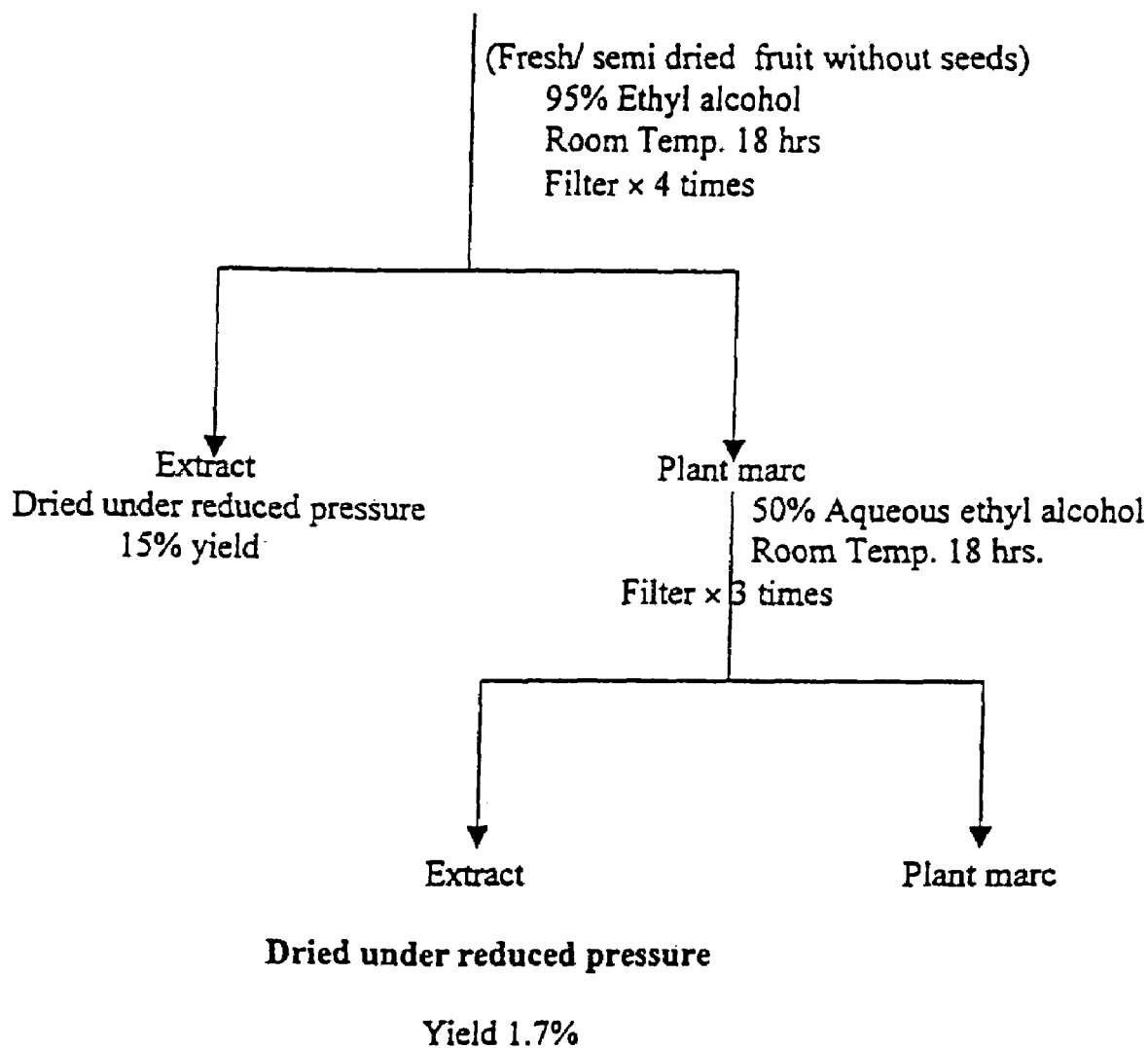
FIG. 6 shows a flow chart for the preparation of extract from fruit *Emblica Officinalis*.

*Emblica officinalis* extract reverses Rifampicin+isoniazid+pyrazinamide induced toxicity. FIG. 5 shows 94% protection against rise in lipid Peroxidation (LPO, liver) and 96% decrease of serum Bilirubin in response to treatment with extract of the present invention.

The invention claimed is:

1. A method of treating CYP 450 and free radical mediated hepatotoxicity caused by at least one anti-TB drug selected from the group consisting of rifampicin, pyrazinamide, and isoniazid so as to restore liver function to normal, comprising:
   (a) providing an orally-administered composition comprising an extract from *Emblica officinalis* and pharmaceutically acceptable additives, said extract comprising from 8.5% to 15% by weight of tannin, said extract and said additives being in the ratio of 1:1–1:10, the additives being selected from a group of nutrients comprising proteins, carbohydrates, sugar, talc, magnesium stearate, cellulose, calcium carbonate, starch-gelatin paste, and/or pharmaceutically acceptable carrier, excipient, diluent, or solvent, wherein said composition treats CYP 450 bio-activated hepatotoxicity induced by at least one anti-TB drug selected from the group consisting of rifampicin, pyrazinamide, and isoniazid so as to restore liver function to normal, but is not effective against hepatotoxicity which is independent of bio-activation by CYP 450
   (b) introducing drug toxicity in hepatocytes of said subject,
   (c) orally administering a hepatocurative dosage of said composition to a subject having said hepatocytes exposed to drug hepatotoxicity, and
   (d) measuring changes in the level of liver/serum markers to estimate hepatocurative effect of the said composition.

2. A method as claimed in claim 1, wherein said composition is in form of capsule, tablet, syrup, concentrate, powder, granule, aerosol, and/or beads.

3. A method as claimed in claim 1, wherein said subject is an animal or human being.

4. A method as claimed in claim 1, wherein said composition controls abnormal rise in the clinical pathological symptoms revealed by serum/liver markers serving as indices of hepatic damage besides control of high levels of Bilirubin.

5. A method as claimed in claim 1, wherein said method uses hepatocyte culture for ideal insight.

6. A method as claimed in claim 1, wherein said drugs are used at cytotoxic levels to produce valid and reproducible results in liver cells.

7. A method as claimed in claim 1, wherein said composition shows restoration of hepatocyte viability.

8. A method as claimed in claim 1, wherein said composition shows about 96% hepatocurative effect against combined effect of rifampicin and isoniazid.

9. A method as claimed in claim 1, wherein said composition shows hepatocurative effect of about 96% against combined effect of rifampicin, isoniazid, and pyrazinamide.

10. A method as claimed in claim 1, wherein said composition shows about 94% hepatocurative effect against rise in lipid Peroxidation (LPO) induced by combination of rifampicin, isoniazid, and pyrazinamide.

11. A method as claimed in claim 1, wherein said composition shows about 96% decrease of serum Bilirubin as a hepatocurative effect against combination of rifampicin, isoniazid, and pyrazinamide.

12. A method as claimed in claim 1, wherein said hepatocurative dosage of said composition is ranging between 50–250 mg/kg.

* * * * *